US008999647B2

(12) United States Patent
Geradts (10) Patent No.: US 8,999,647 B2
(45) Date of Patent: Apr. 7, 2015

(54) METHODS OF SUBCLASSIFICATION OF DUCTAL CARCINOMA IN SITU OF THE BREAST

(75) Inventor: Joseph Geradts, Chapel Hill, NC (US)

(73) Assignee: Duke University, Durham, NC (US)

( * ) Notice: Subject to any disclaimer, the term of this patent is extended or adjusted under 35 U.S.C. 154(b) by 221 days.

(21) Appl. No.: 13/255,558

(22) PCT Filed: Dec. 11, 2009

(86) PCT No.: PCT/US2009/067722
§ 371 (c)(1),
(2), (4) Date: Dec. 12, 2011

(87) PCT Pub. No.: WO2010/104539
PCT Pub. Date: Sep. 16, 2010

(65) Prior Publication Data
US 2012/0094857 A1    Apr. 19, 2012

Related U.S. Application Data

(60) Provisional application No. 61/158,583, filed on Mar. 9, 2009.

(51) Int. Cl.
*C12Q 1/68* (2006.01)
*G01N 33/574* (2006.01)

(52) U.S. Cl.
CPC ............................. *G01N 33/57415* (2013.01)

(58) Field of Classification Search
None
See application file for complete search history.

(56) References Cited

U.S. PATENT DOCUMENTS

| 2004/0191783 | A1 | 9/2004 | Leclercq et al. | |
| 2008/0311573 | A1 | 12/2008 | Lillie et al. | |
| 2009/0280478 | A1* | 11/2009 | Polyak et al. | 435/6 |
| 2012/0094857 | A1 | 4/2012 | Geradts | |

OTHER PUBLICATIONS

Liao et al in "Identification of new breast cancer candidate genes associated with stromal invasion" (Cancer Research: Jan. 15, 2009; vol. 69, Issue 2, Supplement 1:CTRC-AACR San Antonio Breast Cancer Symposium: 2008 Abstracts: Abstract #4036).*
Alexopoulou, A.N., et al., 2010. "Dissecting the transcriptional networks underlying breast cancer: NR4A1 reduces the migration of normal and breast cancer cell lines" Breast Cancer Res 12:R51.
Aubele, M., et al., 2000. "Extensive ductal carcinoma in situ with small foci of invasive ductal carcinoma: Evidence of genetic resemblance by CGH" Int J Cancer 85:82-86.
Bombonati A, Sgroi DC. 2011. "The molecular pathology of breast cancer progression" J Pathol 223:307-317.
Buerger, H., et al., 1999. "Comparative genomic hybridization of ductal carcinoma in situ of the breast-evidence of multiple genetic pathways" J Pathol 187:396-402.
Burstein, H.J., et al., 2004. "Ductal carcinoma in situ of the breast" N Engl J Med 350:1430-1441.
Camacho, C.P., et al., 2010. "Down-regulation of NR4A1 in follicular thyroid carcinomas is restored following lithium treatment" Clin Endocrinol 70:475-483.
Castro, N.P., et al., 2008. "Evidence that molecular changes in cells occur before morphological alterations during the progression of breast ductal carcinoma" Breast Cancer Res 10:R87.
Desouki, M.M., et al., 2010. "Identification of metastasis-associated breast cancer genes using a high-resolution whole genome profiling approach" J Cancer Res Clin Oncol 137:795-809.
Desouki, M.M., et al., 2011. "The genomic relationship between primary breast carcinomas and their nodal metastases" Cancer Invest 29:300-307.
Di Leo, A., et al., 2011. "HER2 and TOP2A as predictive markers for anthracycline-containing chemotherapy regimens as adjuvant treatment of breast cancer: A meta-analysis of individual patient data" Lancet Oncol 12:1134-1142.
Di Pietro, C., et al., 2000. "Genomic localization of the human genes TAF1A, TAF1B and TAF1C, encoding TAF(I)48, TAF(I)63 and TAF(I)110 subunits of class I general transcription initiation factor SL1" Cytogenet Cell Genet 89:133-136.
Eusebi, V., et al., 1994. "Long-term follow-up of in situ carcinoma of the breast" Semin Diagn Pathol 11:223-235.
Farabegoli, F., et al., 2002. "Genetic pathways in the evolution of breast ductal carcinoma in situ" J Pathol 196:280-286.
Fleming, F.J., et al., 2004. "Differential recruitment of coregulator proteins steroid receptor coactivator-1 and silencing mediator for retinoid and thyroid receptors to the estrogen receptor-estrogen response element by beta-estradiol and 4-hydroxytamoxifen in human breast cancer" J Clin Endocrinol Metab 89:375-383.
Frykberg, E.R., et al., 1994. "Overview of the biology and management of ductal carcinoma in situ of the breast" Cancer 74(1 Suppl):350-361.
Fujii, H., et al., 1996. "Genetic progression, histological grade, and allelic loss in ductal carcinoma in situ of the breast" Cancer Res 56:5260-5265.
Gaile, D.P., et al., 2007. "aCGHplus: An R library for the storage, analysis and visualization of aCGH data" Available at: http://sphhp.buffalo.edu/biostat/research/software/acghplus/index.php.
Gaile, D.P., et al., 2010. "iGenomicViewer: R package for visualisation of high dimension genomic data" Int J Bioinform Res Appl 6:584-593.
Geradts et al. "Differential Copy Number Aberrations in New Candidate Genes Associated with Early Breast Cancer Progression" United States and Canadian Academy of Pathology 2009 Annual Meeting Abstract. Mar. 9, 2009. Available on the internet: <http://www.abstracts2view.com/uscap09/view.php?nu=USCAP09L 174>.

(Continued)

*Primary Examiner* — Catherine Hibbert
(74) *Attorney, Agent, or Firm* — Michael Best & Friedrich LLP (57) ABSTRACT

Provided herein are methods of determining the aggressiveness or indolence of a ductal carcinoma in situ lesion. Also provided are methods of developing treatment plans for subjects with a ductal carcinoma in situ lesion based on the aggressiveness of the lesion.

7 Claims, 5 Drawing Sheets

(56) References Cited

OTHER PUBLICATIONS

Ghoshal, P., et al., 2009. "Loss of the SMRT/NCoR2 corepressor correlates with JAG2 overexpression in multiple myeloma" Cancer Res 69:4380-4387.
Green, A.R., et al., 2008. "The prognostic significance of steroid receptor co-regulators in breast cancer: Co-repressor NCOR2/SMRT is an independent indicator of poor outcome" Breast Cancer Res Treat 110:427-437.
Hadjantonakis AK, et al., 1997. "Celsrl, a neural-specific gene encoding an unusual seven-pass transmembrane receptor, maps to mouse chromosome 15 and human chromosome 22qter" Genomics 45:97-104.
Huang, H.Y., et al., 2009. "Persistent uroplakin expression in advanced urothelial carcinomas: Implications in urothelial tumor progression and clinical outcome" Hum Pathol 38:1703-1713.
Hwang, E.S., et al., 2004. "Patterns of chromosomal alterations in breast ductal carcinoma in situ" Clin Cancer Res 10:5160-5167.
Iakovlev, V.V., et al., 2008. "Genomic differences between pure ductal carcinoma in situ of the breast and that associated with invasive disease: A calibrated aCGH study" Clin Cancer Res 14:4446-4454.
James, L.A., et al., 1997. "Comparative genomic hybridisation of ductal carcinoma in situ of the breast: Identification of regions of DNA amplification and deletion in common with invasive breast carcinoma" Oncogene 14:1059-1065.
Jiang, J., et al., 2001. "Identification of two novel human dynein light chain genes, DNLC2A and DNLC2B, and their expression changes in hepatocellular carcinoma tissues from 68 Chinese patients" Gene 281:103-113.
Kurebayashi et al. Expression Levels of Estrogen Receptor-alpha, Estrogen Receptor-beta, Coactivators, and Corepressors in Breast Cancer. Clin Can Res Feb. 2000 vol. 6 No. 2 pp. 512-518.
Leong, A.S., et al., 2001. "Biologic markers in ductal carcinoma in situ and concurrent infiltrating carcinoma. A comparison of eight contemporary grading systems" Am J Clin Pathol 115:709-718.
Li, Q.X., et al. 2006. "NR4A1, 2, 3—An orphan nuclear hormone receptor family involved in cell apoptosis and carcinogenesis" Histol Histopathol 21:533-540.
Ludwig, L., et al., 2003. "Grap-2, a novel RET binding protein, is involved in RET mitogenic signaling" Oncogene 22:5362-5366.
Ludwig, L., et al., 2009. "Expression of the Grb2-related RET adapter protein Grap-2 in human medullary thyroid carcinoma" Cancer Lett 275:194-197.
Matsumoto, K., et al., 2008. "Loss expression of uroplakin III is associated with clinicopathologic features of aggressive bladder cancer" Urology 72:444-449.
Miecznikowski, J.C., et al., 2011. "A new normalizing algorithm for BAC CGH arrays with quality control metrics" J Biomed Biotechnol. Article ID 860732, Epub ahead of print Feb. 21.
Mullican, S.E., et al., 2007. "Abrogation of nuclear receptors Nr4a3 and Nr4a1 leads to development of acute myeloid leukemia" Nat Med 13:730-735.
Nowak, N.J., et al., 2007. "Challenges in array comparative genomic hybridization for the analysis of cancer samples" Genet Med 9:585-595.

O'Connell, P., et al., 1998. "Analysis of loss of heterozygosity in 399 premalignant breast lesions at 15 genetic loci" J Natl Cancer Inst 90:697-703.
Olshen, A.B., et al., 2004. "Circular binary segmentation for the analysis of array-based DNA copy number data" Biostatistics 5:557-572.
Ordentlich et al. "Unique forms of human and mouse nuclear receptor corepressor SMRT" Proc Nat Acad Sci (USA) Mar. 16, 1999 vol. 96 No. 6 pp. 2639-2644.
Pawitan, Y., et al., 2005. "False discovery rate, sensitivity and sample size for microarray studies" Bioinformatics 21:3017-3024.
PCT/US2009/067722 International Search Report dated Mar. 25, 2010 (3 pages).
Peterson, T.J., et al., 2007. "The silencing mediator of retinoic acid and thyroid hormone receptor (SMRT) corepressor is required for full estrogen receptor alpha transcriptional activity" Mol Cell Biol 27:5933-5948.
Polyak, K., et al., 2006. "Do myoepithelial cells hold the key for breast tumor progression?" J Mammary Gland Biol Neoplasia 10:231-247.
Porter et al. "Molecular Markers in Ductal Carcinoma in Situ of the Breast" Mol Cancer Res Mar. 2003 vol. 1 pp. 362-375.
Sanders, M.E., et al., 2005. "The natural history of low-grade ductal carcinoma in situ of the breast in women treated by biopsy only revealed over 30 years of long-term follow-up" Cancer 103:2481-2484.
Shi, Z.Z., et al., 2007. "What we know about ST13, a co-factor of heat shock protein, or a tumor suppressor?" J Zhejiang Univ Sci B 8:170-176.
Silverstein, M.J., et al., 1996. "A prognostic index for ductal carcinoma in situ of the breast" Cancer 77:2267-2274.
Simpson, P.T., et al., 2005. "Molecular evolution of breast cancer" J Pathol 205:248-254.
Song, L., et al., 2005. "Alteration of SMRT tumor suppressor function in transformed non-Hodgkin lymphomas" Cancer Res 65:4554-4561.
van Agthoven, T., et al., 2009. "CITED2 and NCOR2 in anti-oestrogen resistance and progression of breast cancer" Br J Cancer 101:1824-1832.
van de Wiel, M.A., et al., 2007. "CGHcall: Calling aberrations for array CGH tumor profiles" Bioinformatics 23:892-894.
Wang, C., et al., 2009. "Genomic alterations in primary breast cancers compared with their sentinel and more distal lymph node metastases: An aCGH study" Genes Chromosomes Cancer 48:1091-1101.
Wang, L.B., et al., 2005. "Expression of ST13 in colorectal cancer and adjacent normal tissues" World J Gastroenterol 11:336-339.
Wanschers B, et al., 2008. "Rab6 family proteins interact with the dynein light chain protein DYNLRB1" Cell Motil Cytoskeleton 65:183-196.
Westfall, P.H., et al., 1993. "Resampling-Based Multiple Testing: Examples and Methods for P-Value Adjustment" New York: Wiley.
Yu, H., et al., 2007. "Nuclear orphan receptor TR3/Nur77 mediates melanoma cell apoptosis" Cancer Biol Ther 6:405-412.
Yu, J., et al., 2006. "The corepressor silencing mediator for retinoid and thyroid hormone receptor facilitates cellular recovery from DNA double-strand breaks" Cancer Res 66:9316-9322.

* cited by examiner

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
ctgagaccac caggaagagc                                               20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
```

-continued tcctcctcac gatctgcttt                                        20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
tcccagcgtg actcttttct                                        20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
accggtgcta tgaaccagtc                                        20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
gggtagcgtt gttgacatcc                                        20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
acggagaccc cagatttacc                                        20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
gcaggtccct cagttctcac                                        20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
actccaccct caccaaacac                                        20

<210> SEQ ID NO 9
<211> LENGTH: 20
<212> TYPE: DNA

```
<213> ORGANISM: Artificial Sequence
<220> FEATURE:
<223> OTHER INFORMATION: Oligonucleotide

<400> SEQUENCE: 9
cctgtgtggc attaccctct                                           20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide

<400> SEQUENCE: 10
cccctttaag agctgtcacg                                           20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
ccccgacagc tgtaattcat                                           20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
gtcgagcaca aacttcagca                                           20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide

<400> SEQUENCE: 13
ggtgtcctag cagtgggtgt                                           20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide

<400> SEQUENCE: 14
aaagctggag gcaaaagaca                                           20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide

<400> SEQUENCE: 15
gcccacattt tcattttgct                                           20
```

```
<210> SEQ ID NO 16
<211> LENGTH: 20
<212> TYPE: DNA
<213> ORGANISM: Artificial Sequence
<220> FEATURE:
<223> OTHER INFORMATION: Oligonucleotide

<400> SEQUENCE: 16
tgtaagacga aggggtttgg                                              20
```

METHODS OF SUBCLASSIFICATION OF DUCTAL CARCINOMA IN SITU OF THE BREAST

STATEMENT REGARDING FEDERALLY SPONSORED RESEARCH

This invention was made with government support under grant number R21CA 106676-01A1 awarded by the National Cancer Institute. The government has certain rights in the invention.

CROSS-REFERENCE TO RELATED APPLICATIONS

This patent application is a national stage filing under 35 U.S.C. 371 of International Application No. PCT/US2009/067722, filed Dec. 11, 2009, which claims the benefit of priority to U.S. Provisional Application No. 61/158,583, filed Mar. 9, 2009. The disclosure of each application is incorporated by reference herein in its entirety, and priority to each application is hereby claimed.

SEQUENCE LISTING

The sequence listing is filed with the application in electronic format only and is incorporated by reference herein. The sequence listing text file "AS_FILED_Sequence Listing-Text_W000" was created on Dec. 10, 2009, and is 3,312 bytes in size.

BACKGROUND

Ductal carcinomas in situ (DCIS) accounts for about 20% of newly diagnosed breast cancers in the United States amounting to nearly 40,000 cases per year. DCIS is characterized by marked pathologic and clinical heterogeneity. Only a minority of DCIS have the capacity to progress to stromally invasive tumors. From 30-50% of high grade (HG) DCIS lesions progress to invasive carcinoma. In contrast, only about 10-20% of low grade (LG) DCIS progress to an invasive carcinoma. Standard pathologic evaluation does not distinguish DCIS lesions with or without the capacity to progress. In addition, no molecular changes have been identified that reliably differentiate indolent from aggressive DCIS.

As there are no distinguishing features of indolent DCIS, the great majority of patients tend to be over-treated. Patients with a diagnosis of DCIS receive additional surgery, radiation or systemic therapy. Such aggressive treatments are not necessary in 80-90% of LG DCIS and in 50-70% of HG DCIS cases.

SUMMARY OF THE INVENTION

In one aspect, methods of determining the aggressive potential of a ductal carcinoma in situ (DCIS) lesion are provided. The DNA copy number, the level of mRNA expression of a gene or the level of protein expression from a gene in a sample from the DCIS lesion is detected and the results are used to determine the aggressiveness or indolence of the DCIS lesion. The gene may be any or a combination of the genes encoding NR4A1, NCOR2/SMRT, DYNLRB2, TAF1C, GRAP2, ST13, CELSR1, or UPK3A. The results may be used to develop a treatment plan for the subject with the DCIS lesion.

In another aspect, methods for classifying aggressiveness or indolence of a ductal carcinoma in situ (DCIS) lesion are provided. The methods include detecting a DNA copy number of at least one nucleic acid in a cell from the DCIS lesion and using the DNA copy number to classify the aggressiveness or indolence of the DCIS lesion. The nucleic acid is at a human chromosomal location selected from 22q13.1-q13.33, 16q23-q24.2, 12q13-q14 or 12q24-q25.

BRIEF DESCRIPTION OF THE FIGURES

FIG. 3 is a heat map of chromosomal are 22q. The x-axis shows the 20 PD lesions on the left and the 25 MD lesions on the right. The scale on the right indicates the −log 10 P-values for differential amplification (red) or deletion (green) in the two groups. The y-axis shows the chromosomal location from the telomere (top) to the centromere (bottom). Near the telomere gains are more common in PD. The remainder of the arm shows higher frequencies of deletions in MD lesions.

DETAILED DESCRIPTION

The Examples below demonstrate that the DNA copy number of particular genes found in particular regions of several chromosomes are likely to be altered in ductal carcinoma in situ (DCIS) lesions and that the copy number of the gene in cells from the lesion is indicative of the aggressiveness of the cancer. The Examples demonstrate ductal carcinoma invasiveness can be predicted by analysis of the DNA copy number at a human chromosomal location selected from 22q13.1-q13.33, 16q23-q24.2, 12q13-q14 or 12q24-q25. The DNA copy number was shown to be increased in indolent DCIS at 22q13.1-q13.33, 16q23, 12q13-q14 or 12q24-q25 relative to controls. The DNA copy number was more likely to be increased at 22q13.1 relative to controls in DCIS lesions that were aggressive and likely to become invasive. The DNA copy number was more likely to be reduced at 16q23, 12q13-q14 or 12q24-q25 in aggressive DCIS lesions relative to controls. The DNA copy number was more likely to be reduced at 16q24.1 in indolent DCIS relative to controls.

Control or normal cells are expected to have two alleles of each gene. Four or more copies of a gene is considered an increase relative to control cells and one or no copies of a gene is considered as a decrease in copy number relative to controls. The number of DNA copies of the gene can be detected in a sample from the DCIS lesion.

The sample may be obtained by any means available to those skilled in the art including, but not limited to, a biopsy of the DCIS lesion, including a needle biopsy or surgical removal of tissue containing the lesion. Breast tissues with DCIS generally contain normal cells as well as neoplastic cells. In the Examples, the cells used in the samples for preparation of the DNA for aCGH were microdissected to ensure that only DCIS cells were included. As noted in the Examples, the gene copy number may be assessed in samples including both DCIS cells and normal cells. The percentage of DCIS vs. normal cells can be used to calculate whether the DCIS cells have a change in gene copy number as compared to non-neoplastic cells.

Gene copy number may be assessed by any method, including methods known to those of skill in the art. For example the gene copy number may be assessed by methods, including but not limited to, array comparative genomic hybridization (aCGH), in situ hybridization (ISH, e.g., fluorescent (FISH) or chromogenic (CISH)), microarray analysis and real time quantitative PCR. Control cells for comparison may be normal, non-neoplastic cells from the same or a different subject or may be cancer cells with known genomic DNA changes and defined aggressiveness. As noted above, when assessing gene copy number, control cells are not needed for comparison due to the diploid nature of the human genome.

Several specific genes whose gene copy number was predictive of the DCIS lesion's aggressiveness (i.e. the propensity of a lesion to become invasive) were also identified in the Examples. In particular, increased copy number of NCOR2/SMRT (chromosome location 12q24.31), NR4A1 (chromosome location 12q13), DYNLRB2 (chromosome location 16q23.3), CELSR1 (chromosome location 22q13.31), UPK3A (chromosome location 22q13.31) or ST13 (chromosome location 22q13.1) was shown to be indicative of indolent or non-aggressive DCIS lesions. Conversely a decreased copy number of NCOR2/SMRT, NR4A1, DYNLRB2 was indicative of increased aggressiveness and a higher likelihood of invasiveness. A decrease in ST13 copy number was indicative of an indolent lesion. An increase in GRAP2 (chromosome location 22q13.1) copy number in a DCIS cell was indicative of increased aggressiveness. A reduced copy number of TAF1C (chromosome location 16q24.1) in a DCIS lesion was indicative of an indolent lesion. The GenBank NCBI and Ensembl Gene ID No. for the genes are included in Table 1.

by Northern blot or quantitative rtPCR, or at the level of protein expression, e.g. by Western blot, ELISA, immunohistochemistry (IHC) or functional protein assays. Other methods of assessing gene expression or protein expression may also be used, including additional methods known to those skilled in the art.

The DCIS lesion may be classified or predicted to be aggressive or indolent based on analysis of the DNA copy number, mRNA expression or protein expression of a single gene, the combination of all eight genes, or a sub-combination of a portion of the eight genes identified herein. As shown in the examples below, detection of a change in DNA copy number, mRNA levels or protein levels of one of the genes described herein may be capable of predicting the likelihood of invasive carcinoma. Evaluation of NCOR2/SMRT alone could be used to determine the aggressiveness of the lesion. Evaluation and detection based on all eight genes identified herein was capable of determining the aggressiveness of the lesion with an AUC of 0.946. In addition, at least one set of five genes including NR4A, NCOR2/SMRT, DYNLRB2, GRAP2, and CELSR1 was capable of predicting the aggressiveness of the lesion with an AUC of 0.953. Any combination of the eight genes may be used in the methods described herein.

The determination of the aggressiveness phenotype of the DCIS lesion may be used to develop a treatment plan for the subject with the DCIS lesion. As noted above, most DCIS is indolent, but due to the propensity of some DCIS to become invasive many subjects with DCIS are treated aggressively. A reliable test to determine the propensity of a DCIS lesion to progress to invasive cancer would save many patients from undergoing needless procedures and would reduce health care costs. Those subjects whose lesions are likely indolent may be treated by monitoring the lesion over time. Those subjects whose lesions are likely aggressive can receive aggressive therapy, such as surgery, radiation, chemotherapy or a combination thereof. Thus, the results of the methods provided herein may be used to develop treatment plans for the subject or may be used as a prognostic assay to provide physicians with additional information.

TABLE 1

GenBank and Ensembl Gene ID No.

| | Gene | | | |
| --- | --- | --- | --- | --- |
| | NR4A1 | NCOR2 | DYNLRB2 | TAF1C |
| NCBI: GeneID: | 3164 | 9612 | 83657 | 9013 |
| Ensembl Gene ID | ENSG00000123358 | ENSG00000196498 | ENSG00000168589 | ENSG00000103168 |
| | Gene | | | |
| | GRAP2 | ST13 | CELSR1 | UPK3A |
| NCBI: GeneID: | 9402 | 6767 | 9620 | 7380 |
| Ensembl Gene ID | ENSG00000100351 | ENSG00000100380 | ENSG00000075275 | ENSG00000100373 |

As demonstrated in the Examples, overexpression of genes as evidenced by increased mRNA or protein levels due to increased gene copy number or conversely, reduced expression of genes as evidenced by decreases in mRNA or protein levels due to reduced gene copy number may be indicative of the aggressiveness or invasive potential of the DCIS lesion. Therefore, the mRNA or protein expression level of the genes as compared to control cells may also be used to assess the aggressiveness of the DCIS lesion. Gene expression levels may be assessed either at the level of mRNA expression, e.g.

EXAMPLES

Low grade (LG) DCIS cases were selected for analysis. For these studies low-grade DCIS was defined as nuclear grade 1 or 2 with no necrosis apparent. Of the 116 cases of formalin fixed, paraffin embedded (FFPE) LGDCIS samples selected, 61 of them contained a small invasive component, indicating aggressive potential (MD=mixed DCIS, MI=mixed invasive carcinoma) and 55 cases showed no evidence of invasion within at least 5 years (PD=pure DCIS). These samples were from the surgical pathology files of Duke University Medical Center (DUMC) and Roswell Park Cancer Institute (RPCI). The three different types of lesions were microdissected using laser capture microdissection (over 200 paraffin blocks; 10 μm sections), genomic DNA was extracted, and 118 array comparative genomic hybridization (aCGH) hybridizations were performed utilizing high density (19 k) bacterial artificial chromosome (BAC) arrays (average genomic resolution was 170 kb). The arrays were custom made by the RPCI Genomics Core Facility. The DNA quality was assessed via the Enzo BioScore Assay and samples with poor DNA quality were not used for further analysis.

Figure 1:
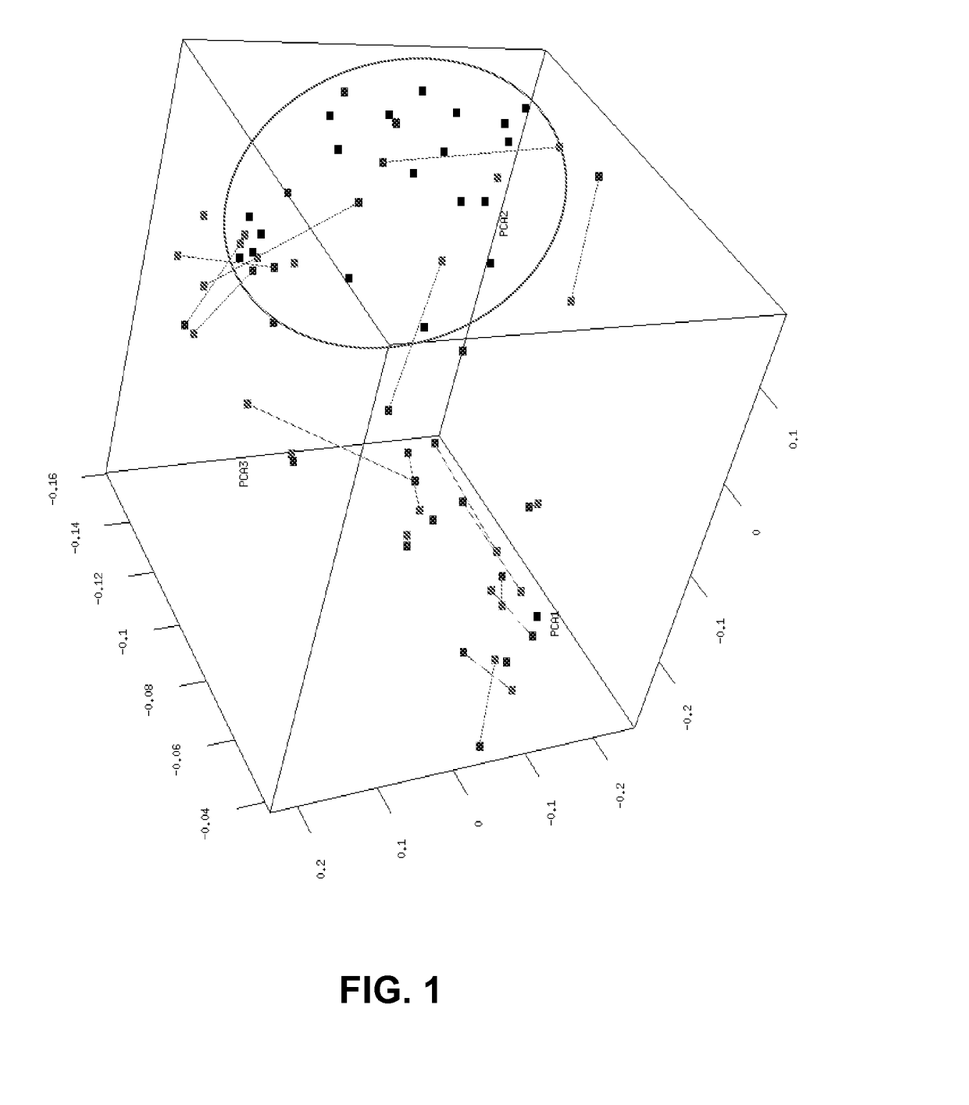
FIG. 1 is a three-dimensional graphical plot showing the principal component analysis (PCA) for 20 PD (black), 25 MD (blue) and 24 MI (red) lesions (where PD indicates pure (indolent) DCIS, MD mixed (aggressive) DCIS, and MI matched invasive carcinoma). 18 cases had both an MD and MI component and are connected by lines. The circle contains all but one of the PD lesions, indicating that they share genomic alterations that set them apart from the aggressive (MD) DCIS lesions.
Figure 2A:
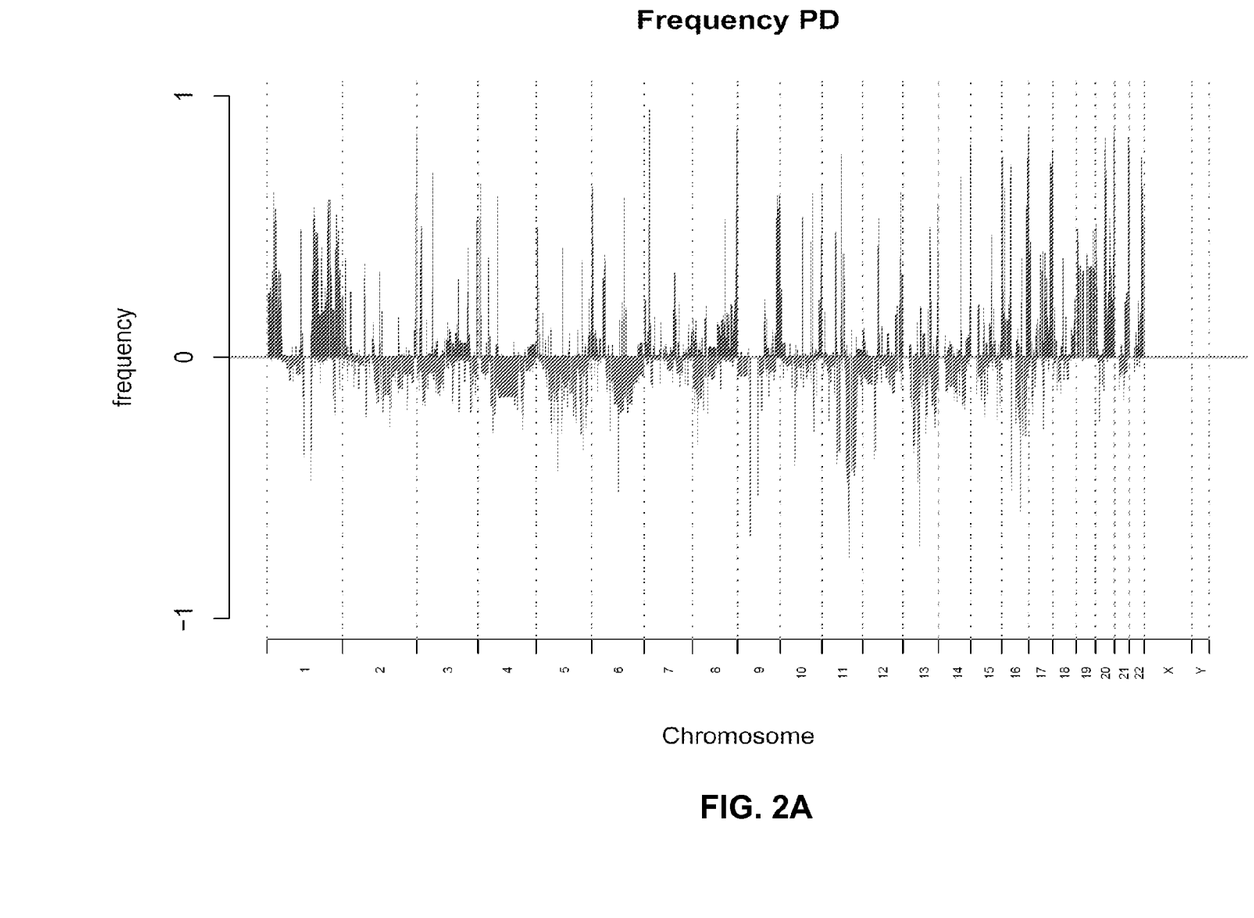
FIG. 2 is a set of graphs showing the DNA copy number changes in PD (A) and MD (D) lesions by their chromosomal location.
Figure 2B:
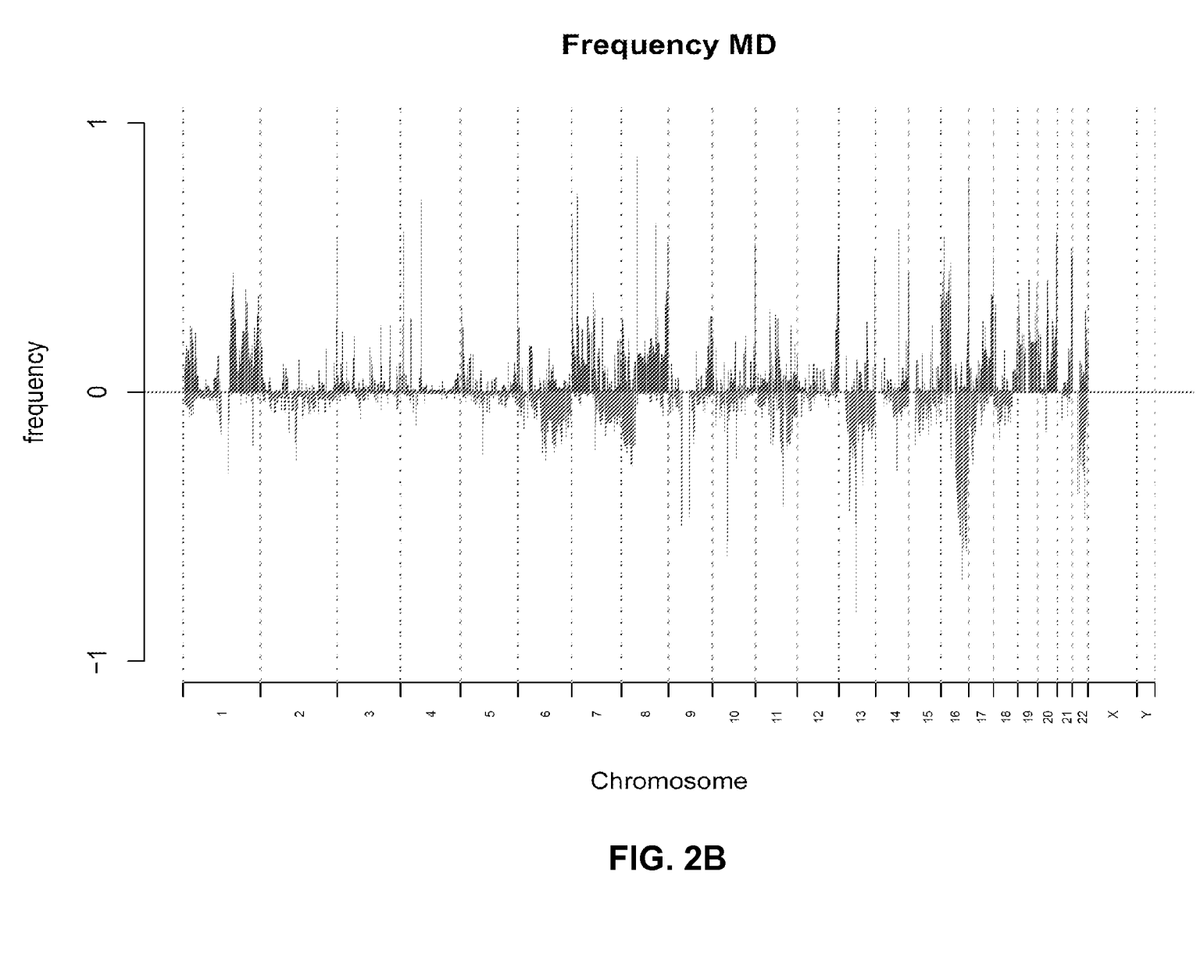

Sixty-nine of the 118 aCGH hybridizations yielded interpretable DNA profiles: 20 PD, 25 MD, 24 MI ("Cohort 1"). Statistical analyses were performed using the generic GCH Call program. Surprisingly, while paired in situ and invasive carcinomas had comparable frequencies of DNA copy number gains and losses, pure intraductal carcinomas were characterized by a larger number of copy number changes, especially gains (Table 2). Moreover, Principal component analysis (PCA) showed that the "indolent" DCIS lesions clustered separately from the mixed carcinomas (circled area in FIG. 1). FIG. 2 demonstrates that 17 regions on 13 chromosomal arms contained differential copy number aberrations (CNAs), almost all of which occurred more commonly in pure (indolent) DCIS lesions. The majority of these differential CNAs were DNA gains.

TABLE 2

DNA copy number frequencies in low grade DCIS with and without associated invasive ductal carcinoma (IDC)

| | N | Average copy number gains | Average copy number losses | Average total copy number changes |
|---|---|---|---|---|
| DCIS without IDC [PD] | 20 | 8.4% | 8.2% | 16.6% |
| DCIS with IDC [MD] | 25 | 6.3% | 5.5% | 11.8% |
| Matched IDC [MI] | 24 | 6.9% | 6.1% | 13.0% |
| TOTAL | 69 | 7.0% | 6.5% | 13.5% |

Figure 3:
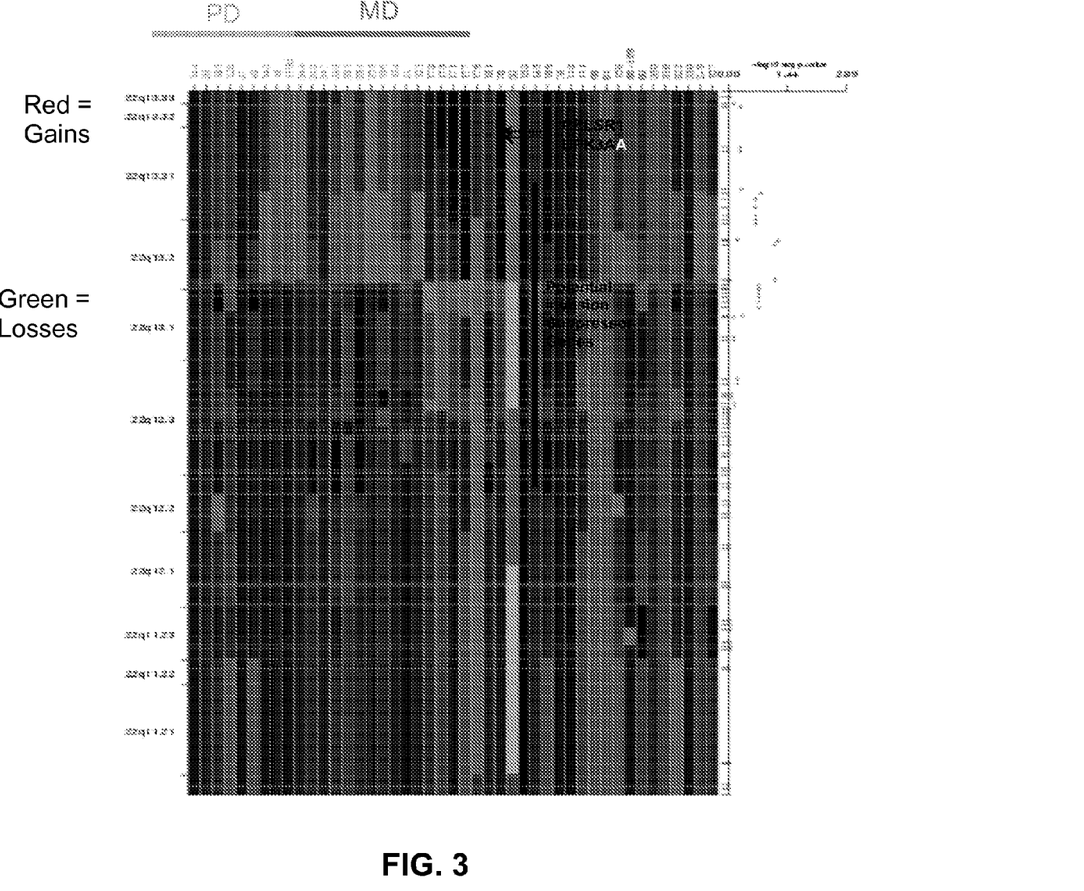

FIG. 3 details the differential copy number changes on chromosome 22q. Only this chromosomal arm contained a higher frequency of copy number losses in the MD group, suggesting possible inactivation of invasion suppressor genes on that chromosomal arm. From the 17 differentially amplified or deleted regions, 19 candidate genes were selected for further validation studies, based on statistical probability and functional interest. Of those, 8 were confirmed to be differentially amplified or deleted in PD versus MD lesions, utilizing quantitative (Q-)PCR on aliquots of genomic DNA. The primers used for the PCR are provided in Table 3. These 8 genes and the data obtained are summarized in Table 4. Of note, three of these genes have not been implicated in human neoplasia before, and only SMRT was previously described in human breast cancer.

TABLE 3

Primers used for PCR

| Gene | OLIGO | Sequence | | Amplicon | Tm |
|---|---|---|---|---|---|
| NR4A1 | Forward | CTGAGACCACCAGGAAGAGC | (SEQ ID NO: 1) | | 59.99 |
| | Reverse | TCCTCCTCACGATCTGCTTT | (SEQ ID NO: 2) | 99 | 59.95 |
| NCOR2 | Forward | TCCCAGCGTGACTCTTTTCT | (SEQ ID NO: 3) | | 59.99 |
| | Reverse | ACCGGTGCTATGAACCAGTC | (SEQ ID NO: 4) | 90 | 60 |
| DYNLRB2 | Forward | GGGTAGCGTTGTTGACATCC | (SEQ ID NO: 5) | | 60.38 |
| | Reverse | ACGGAGACCCCAGATTTACC | (SEQ ID NO: 6) | 93 | 60.19 |
| TAF1C | Forward | GCAGGTCCCTCAGTTCTCAC | (SEQ ID NO: 7) | | 59.84 |
| | Reverse | ACTCCACCCTCACCAAACAC | (SEQ ID NO: 8) | 84 | 59.86 |
| Grap2 | Forward | CCTGTGTGGCATTACCCTCT | (SEQ ID NO: 9) | | 59.99 |
| | Reverse | CCCCTTTAAGAGCTGTCACG | (SEQ ID NO: 10) | 80 | 59.87 |
| ST13 | Forward | CCCCGACAGCTGTAATTCAT | (SEQ ID NO: 11) | | 59.96 |
| | Reverse | GTCGAGCACAAACTTCAGCA | (SEQ ID NO: 12) | 88 | 60.18 |
| CELSR1 | Forward | GGTGTCCTAGCAGTGGGTGT | (SEQ ID NO: 13) | | 60.03 |
| | Reverse | AAAGCTGGAGGCAAAAGACA | (SEQ ID NO: 14) | 90 | 59.99 |
| UPK3A | Forward | GCCCACATTTTCATTTTGCT | (SEQ ID NO: 15) | | 59.94 |
| | Reverse | TGTAAGACGAAGGGGTTTGG | (SEQ ID NO: 16) | 100 | 59.96 |

TABLE 4

Differential copy number changes in low grade DCIS with (MD) and without (PD) associated stromal invasion: Eight candidate genes validated by Q-PCR

| Candidate Gene | Chr. Loc. | Differential CNA | Function | Involvement in Human Neoplasia |
|---|---|---|---|---|
| SMRT (NCOR2) | 12q24.31 | More commonly amplified in PD, more commonly deleted in MD | Component of repressing nuclear receptor complex; involved in DNA repair | Expression correlated with breast cancer recurrence |
| NR4A1 | 12q13.13 | More commonly amplified | Nuclear steroid hormone | Downregulated in |

TABLE 4-continued

Differential copy number changes in low grade DCIS with (MD) and without (PD) associated stromal invasion: Eight candidate genes validated by Q-PCR

| Candidate Gene | Chr. Loc. | Differential CNA | Function | Involvement in Human Neoplasia |
|---|---|---|---|---|
| (Nur77) | | in PD, more commonly deleted in MD | receptor; pro-apoptotic | AML and in follicular thyroid ca |
| DYNLRB2 (DNLC2B) | 16q23.2 | More commonly amplified in PD, more commonly deleted in MD | Dynein light chain protein | Downregulated in liver cancer |
| TAF1C | 16q24.1 | More commonly deleted in PD | Transcription co-factor | Not described |
| CELSR1 | 22q13.31 | More commonly amplified in PD | Flamingo-type cadherin; component of Wnt signaling pathway | Not described |
| UPK3A | 22q13.31 | More commonly amplified in PD | Cell membrane protein; involved in urothelial differentiation | Downregulation associated with worse prognosis in bladder cancer |
| ST13 (HIP) | 22q13.1 | More commonly amplified or deleted in PD | Hsp70 co-chaperone | Downregulated in colon cancer |
| GRAP2 | 22q13.1 | More commonly amplified in MD | Involved in TCR signaling | Not described |

Figure 4:
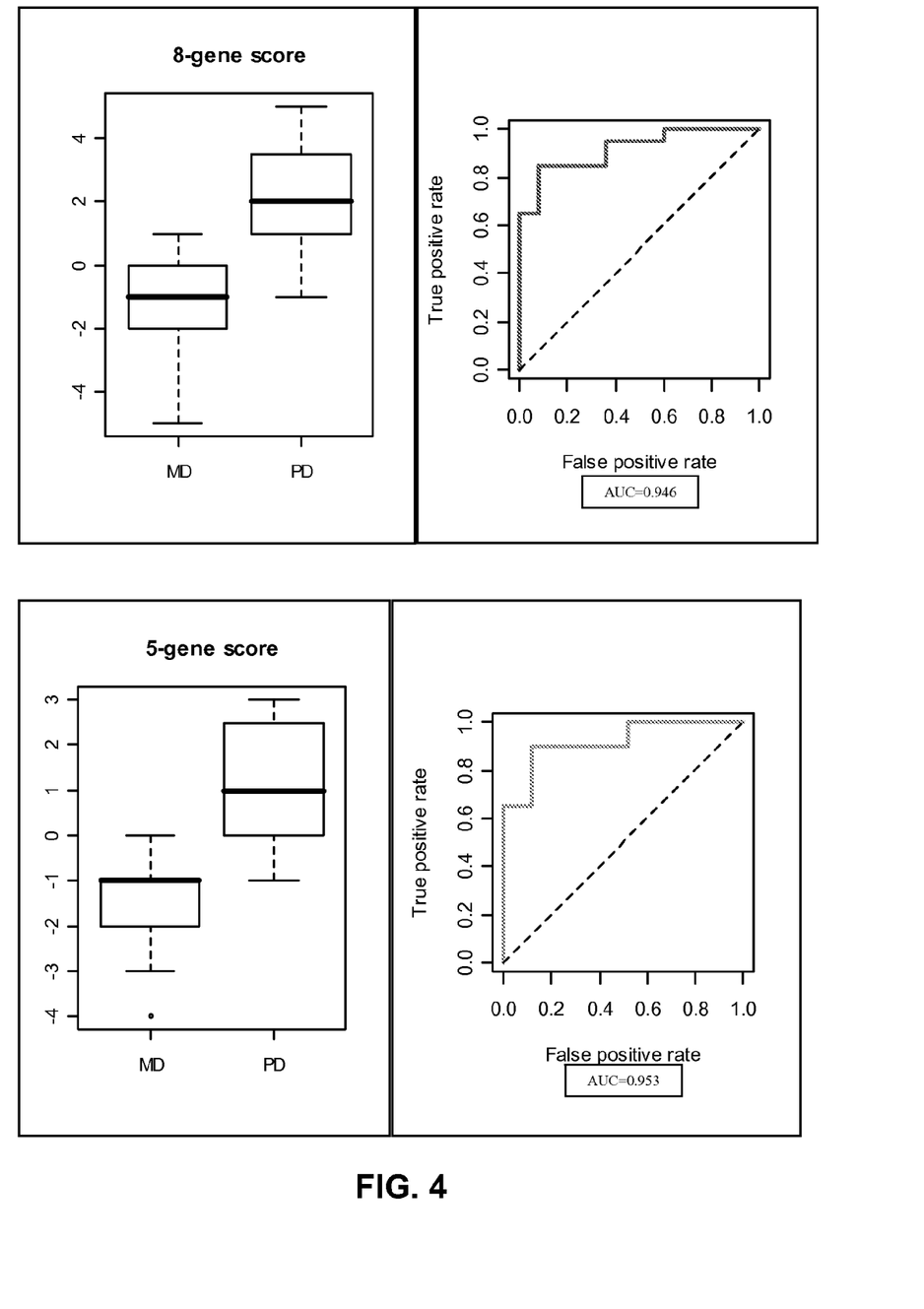
FIG. 4 is a set of graphs showing the analysis of the DNA copy number experiments using 5 and 8 genes combinations and the ROC curves and AUCs for these experiments.

Statistical analysis of the Q-PCR data showing the ROC curves and the AUC for combinations of 5 or 8 of the identified genes demonstrates that a change in gene copy number of at least 5 of these genes can discriminate between indolent and aggressive DCIS with high accuracy (FIG. 4).

Because SMRT was the gene with the single highest discriminatory power, its differential copy number distribution was confirmed in an independent series of PD and MD lesions ("Cohort 2") using quantitative PCR. Cohort 2 consisted of 10 ng samples from microdissected cells from a separate set of 18 PD and 17 MD lesions. The PCR assay sensitivity cut-off was +1.0 for gains and −0.5 for losses (log 2 ratios). GAPDH was used as a reference gene. Table 5 details the results of three experiments. Each experiment demonstrated that SMRT gains were more common in PD lesions. In addition, the Q-PCR experiments revealed a much higher frequency of allele loss in the MD group. These findings suggest that SMRT may act as an invasion suppressor: it may be activated in DCIS lesions that do not have the capacity to invade and inactivated in lesions that do progress.

TABLE 5

SMRT copy number changes in PD vs. MD

| | PD | | | MD | | | |
|---|---|---|---|---|---|---|---|
| | Loss | Normal | Gain | Loss | Normal | Gain | P-Value* |
| aCGH Cohort 1 | 0 | 5 | 15 | 2 | 17 | 6 | 0.0028 |
| Q-PCR Cohort 1 | 6 | 10 | 4 | 22 | 3 | 0 | 0.0003 |
| Q-PCR Cohort 2 | 4 | 10 | 4 | 11 | 6 | 0 | 0.0182 |

*Unordered Kruskal-Willis test

Gene copy number changes may correlate with a change in gene expression as measured by mRNA and/or protein expression levels in the cell. To test whether the protein expression levels correlated with the gene copy number immunohistochemistry (IHC) assays were performed on the tissue sections for NCOR2/SMRT protein levels. The paraffin sections were reacted with mouse monoclonal antibody 1542/H7 from Santa Cruz at 2 μg/ml for 1 hour. The detection reaction utilized the Bond Refine horseradish peroxidase system from Leica.

The results are shown in Table 6. Although the changes are not statistically significant due to the small number of interpretable samples (n=30), the results correlate to those obtained by aCGH and Q-PCR. The data suggest that NCOR2/SMRT levels are increased in a higher proportion of PD lesions (30% vs. 10%) and reduced or absent in a higher proportion of MD lesions (20% vs. 10%).

TABLE 6

IHC of PD and MD lesions for NCOR2/SMRT protein levels

| DCIS Type | No/Reduced Expression | Normal Expression | Increased Expression |
|---|---|---|---|
| PD | 1 | 6 | 3 |
| MD | 4 | 14 | 2 |

Prophetic Examples

In the Examples above, pure populations of DCIS cells were isolated via laser capture microdissection of paraffin sections, and genomic DNA was prepared and assayed from those preparations following routine protocols. For each of the 8 genes comprising the "invasion signature", appropriate primers and Q-PCR protocols were designed. GAPDH was used as a reference gene with normal copy number and defined thresholds of gains of at least two alleles, and of losses of at least one allele. However, tissue microdissection is laborious and requires specialized equipment. Whole tissue sections from the same cohort of cases from which the signature was derived will be used to determine if microdissection is necessary. Briefly, from whole tissue sections, genomic DNA will be extracted in the same fashion, and Q-PCR experiments will be performed using the established protocols. Because the tumor DNA will be diluted by DNA from non-neoplastic cells, the amplitude of copy number gains and losses is expected to be lower for each case. To account for this effect and to set appropriate thresholds that define copy number gains and losses, we will perform dilution curves for each gene. One sample with a 2× copy number, and another one with a defined loss of one allele, will be diluted with DNA extracted from formalin fixed, paraffin embedded normal human breast tissue to yield ratios of 25%, 50%, and 75%, reflecting the typical range of tumor cellularity in whole tissue sections. The evaluation of copy number over the various dilutions will be observational, and descriptive statistics and Spearman rank correlation will be used to determine threshold values for copy number losses and gains.

The differential copy number gains and losses were defined using LGDCIS. We hypothesize that similar molecular changes exist in HGDCIS lesions (i.e., intraductal carcinomas with a nuclear grade of 3) as well. To this end, we will utilize 50 HGDCIS cases from the DUMC files and/or from other sources. The experiments and statistical analysis will be performed as described above.

A chromogenic in situ hybridization (CISH) assay for all 8 genes will be developed. This technique also detects DNA copy number changes, but allows evaluation specifically of the neoplastic cell population. The procedure for CISH is very similar compared to the more commonly used FISH technique, except that the detection reaction utilizes chromogenic substrates instead of fluorescent dyes. CISH has several advantages, including use of brightfield microscopy and permanence of the signals. These assays may be routinely performed in a diagnostic laboratory. For each of the 8 genes, we will construct appropriate biotinylated oligonucleotide probes (Integrated DNA Technologies, Skokie, Ill.). We will employ the Dako GenPoint kit to detect the presence or absence of specific hybridization (Dako, Carpinteria, Calif.). Briefly, the slides will be deparaffinized and heated in target retrieval buffer (sub-boiling for 20 min). They will be quenched in 3% $H_2O_2$ in methanol for 20 min. The DNA will be denatured at 95° C. for 5 min. For each biotinylated oligonucleotide probe, the optimal hybridization and stringent wash temperature will be determined. After incubation in the hybridizer instrument, the washed slides will be reacted with primary strepatavidin-HRP solution for 15 min. A subsequent amplification step utilizes biotinyl tyramide (15 min) This will be followed by a second streptavidin-HRP step (15 min) The chromogenic reaction utilizes DAB (5 min) Finally, the slides will be counterstained with hematoxylin and mounted for light microscopic evaluation. For any given gene, the number of signals in each tumor cell will be counted. We will evaluate 100 DCIS cells per case. An average signal number of 4 or more per cell will count as a gain; an average signal number of 1 or less will count as a loss. As controls, we will use benign tissues from non-cancer patients. Normal cells should contain 2 copies of each gene. Negative control reactions will be performed without DNA probes. When all genes have been scored in all samples, statistical analysis will be performed to determine which combination of the 8 genes has the highest power of differentiating DCIS cases with and without the capacity to invade the stroma, using the same additive and multivariate models described above.

As an alternate in situ technique we will employ IHC, which interrogates gene expression at the protein level. It is reasonable to expect that DNA copy number gains will be associated with increased, and losses with decreased, levels of the corresponding protein product. For 7 of the 8 genes in our panel, commercial antibodies are available (at present, no antibodies exist against DYNLRB2). We previously used the SMRT antibody to develop an IHC assay to study expression of that gene in invasive breast carcinomas; we found down-regulation or loss in 80% of cases. Indeed, in the Examples above the SMRT protein levels were found to correlate to the gene copy number. Briefly, 5 µm paraffin sections are dewaxed and rehydrated. For each antibody, the optimal antigen retrieval method (e.g. enzymatic, heat induced, combination) is established. The optimal antibody titer and incubation time and temperature are determined, using known positive and negative controls. These include numerous well characterized human cancer cell lines that have been fixed and paraffin embedded, as well as a large number of archival normal and neoplastic tissues. Several different detection methods are available. We routinely use peroxidase based detection systems including the Vectastain Elite ABC kit (Vector), the mouse and rabbit Envision kits (Dako), and the LSAB kit (Dako). For antigens expressed at low levels, we can employ a signal amplification step (Dako). DAB is used as chromogen and hematoxylin as counterstain. Nonspecific species-matched antibodies are used in negative control reactions. Evaluation of the IHC stains will take into account the subcellular localization, percentage of staining cells, staining pattern (diffuse, mosaic, patchy, focal) and staining intensity.

The invention claimed is:

1. A method of determining the aggressiveness of a ductal carcinoma in situ (DCIS) lesion of the breast comprising:
   (a) detecting the DNA copy number of CELSR1 in a sample from the DCIS lesion of the breast, wherein the DNA copy number is detected by array comparative genomic hybridization (aGCH), quantitative PCR, or in situ hybridization;
   (b) comparing the DNA copy number of CELSR1 in the sample against a normal DNA copy number of CELSR1, wherein the normal DNA copy number of CELSR1 is two;
   (c) determining the aggressiveness of the DCIS lesion based on the comparison in step (b), wherein an increased DNA copy number of CELSR1 is indicative of an indolent DCIS lesion.

2. The method of claim 1, wherein the sample is a DCIS cell.

3. The method of claim 1, wherein the sample includes cells not from the DCIS lesion.

4. The method of claim 1, further comprising detecting in the sample the DNA copy number of a gene selected from the group consisting of NR4A1, NCOR2/SMRT, DYNLRB2, TAF1C, GRAP2, ST13, and UPK3A.

5. The method of claim 4, wherein the DNA copy number of NR4A1, NCOR2/SMRT, DYNLRB2, TAF1C, GRAP2, ST13, UPK3A, and CELSR1 are detected.

6. The method of claim 4, wherein the DNA copy number of NR4A1, NCOR2/SMRT, DYNLRB2, GRAP2, and CELSR1 are detected.

7. The method of claim 4, wherein
   (a) an increased DNA copy number of NR4A1, NCOR2/SMRT, DYNLRB2, or UPK3A is indicative of an indolent DCIS lesion;
   (b) a decreased copy number of NR4A1, NCOR2/SMRT, or DYNLRB2 is indicative of an aggressive DCIS lesion;
   (c) an increased DNA copy number of GRAP2 is indicative of an aggressive DCIS lesion;
   (d) a decreased DNA copy number of TAF1C is indicative of an indolent DCIS lesion; or
   (e) a change in the DNA copy number of ST13 is indicative of an indolent DCIS lesion.

* * * * *